(12) United States Patent  
Lambridis et al.

(10) Patent No.: US 9,119,454 B2  
(45) Date of Patent: Sep. 1, 2015

(54) PRESSED COSMETIC POWDER CAKE DEVICES AND METHODS

(71) Applicant: Mana Products, Inc., Long Island City, NY (US)

(72) Inventors: George Lambridis, Wayne, NJ (US); Chris Raftis, Bayside, NY (US); Julio Pena, Woodside, NY (US)

(73) Assignee: MANA PRODUCTS, INC., Long Island City, NY (US)

(*) Notice: Subject to any disclaimer, the term of this patent is extended or adjusted under 35 U.S.C. 154(b) by 0 days.

(21) Appl. No.: 14/049,782

(22) Filed: Oct. 9, 2013

(65) Prior Publication Data

US 2015/0096581 A1    Apr. 9, 2015

(51) Int. Cl.  
*A45D 33/00* (2006.01)

(52) U.S. Cl.  
CPC .......... *A45D 33/006* (2013.01); *A45D 33/003* (2013.01); *A45D 33/008* (2013.01)

(58) Field of Classification Search  
CPC ... A45D 33/33; A45D 33/006; A45D 33/003; A45D 33/008; A45D 33/18; A45D 40/00; A45D 2034/007; A61K 8/00; A61K 8/0216  
USPC .......................... 132/303, 304, 305, 293, 296; 401/126–130  
See application file for complete search history.

(56) References Cited

U.S. PATENT DOCUMENTS

| | | | |
|---|---|---|---|
| 1,902,681 A * | 3/1933 | Tuttle et al. ................... | 132/315 |
| 3,837,749 A * | 9/1974 | Spatz ............................ | 401/130 |
| 4,337,859 A | 7/1982 | Murphy et al. | |
| 4,714,084 A | 12/1987 | Berry et al. | |
| 4,820,518 A | 4/1989 | Murphy et al. | |
| 4,828,419 A * | 5/1989 | Porter et al. .................. | 401/126 |
| 5,002,415 A * | 3/1991 | Gueret ......................... | 401/126 |
| 5,096,319 A * | 3/1992 | Gueret ......................... | 401/126 |
| 5,205,431 A | 4/1993 | Zinnbauer | |
| 5,709,232 A | 1/1998 | Sheffler et al. | |
| 5,873,670 A * | 2/1999 | Spivey et al. ................. | 401/126 |
| 6,245,341 B1 | 6/2001 | Pahlck et al. | |
| 2003/0010350 A1 | 1/2003 | De Laforcade | |
| 2004/0173498 A1 | 9/2004 | Lee | |
| 2005/0109661 A1 | 5/2005 | Shih | |

FOREIGN PATENT DOCUMENTS

WO    2013/065951 A1    5/2013

* cited by examiner

*Primary Examiner* — Robyn Doan  
(74) *Attorney, Agent, or Firm* — Brian R. Pollack; Day Pitney LLP

(57) ABSTRACT

A cosmetic product including a pressed cosmetic powder cake is provided. The pressed cosmetic powder cake includes depression formed therein for receiving a liquid to facilitate use of the cosmetic product. The pan defines a recess therein for holding the powder cake. The cosmetic case includes a base portion for receiving the pan and a lid that may be coupled to one another by a hinge.

11 Claims, 23 Drawing Sheets

PRESSED COSMETIC POWDER CAKE DEVICES AND METHODS

CROSS-REFERENCE TO RELATED APPLICATIONS

This application is related to U.S. Design application Ser. No. 29/468,950 filed Oct. 4, 2013, the disclosure of which is incorporated herein by reference in its entirety for any purpose whatsoever.

BACKGROUND

1. Field of the Disclosed Embodiments

The disclosed embodiments relate to cosmetic products, including pressed cosmetic powder cakes and corresponding containers and embodiments of a cosmetic case in which the corresponding container is inserted into.

2. Background of the Disclosure

A variety of cosmetic products including pressed powder cakes and the like are known in the art. The present disclosure provides devices and methods that advance over the current state of the art.

SUMMARY OF THE DISCLOSED EMBODIMENTS

In general, in a first aspect, the disclosure features a cosmetic product, including a pressed cosmetic powder cake. The pressed cosmetic powder cake has a depression formed into the cake, such as proximate the center of an upper surface of the cake for receiving a predetermined amount of a liquid. The product further includes a pressed powder cake pan. The pan includes a recess to receive the powder cake. The product also includes a cosmetic case that includes a lower body portion or base and an upper body portion or lid that can be coupled at a hinge, if desired. The lower body portion or base defines an interior cavity therein to receive the powder cake pan.

If desired, the lower body portion or base of the container can be configured with a receiving groove formed integrally in the inner circumference of the lower body portion or base. The upper body portion or lid can be configured with an inner surface for receiving a mirror. If desired, the upper body portion or lid can be configured with an outwardly protruding sealing member formed integrally on the outer circumference of the upper body portion or lid. The receiving groove can be configured to receive the outwardly protruding sealing member of the upper body portion or lid allowing for the cosmetic container to be in a closed position.

Pressed powder products, such as face powder, eye shadow, blushes or the like have effectively replaced conventional loose powder products. Pressed powder products are produced by compressing loose powder into a metal pan using direct pressure. To make the water and powder mixing task easier for the user when using a brush or sponger application, in one aspect, the disclosure provides a pressed powder cake that is formed with a depression in the pressed powder cake to receive a liquid or other material containing liquid (e.g., gel), preferably water. Such depressions can be made with a die of a press, preferably the same press that is used to make the powder cake such that the powder cake and depression are formed during a single operation. The press thus forms a "well" or reservoir in the main body of the pressed powder cake where water droplets can be deposited. The well can be provided with concave walls, as desired, that act to confine the water droplet(s) being placed in the well and prevent the water from rolling off of the pressed powder cake, thereby facilitating use. This is of particular utility when the pressed powder cake is formed from hydrophobic material, which is common. The well can be provided in a variety of shapes and sizes, where the measured diameters, areas, widths or lengths of the depression is a percentage of the overall diameters, areas, widths or lengths of the top surface of the pressed powder cake. For example, round shaped depressions can be configured with a diameter from about 5 percent to about 95 percent of the overall diameter of a round pressed powder cake, in any desired increment of one percent, such as six, seven, eight percent, and so on. The well can have a geometric center in a horizontal plane that coincides with a center of the pressed powder cake in the horizontal plane. In other embodiments, the well can have a geometric center in a horizontal plane that does not coincide with a geometric center of the pressed powder cake in the horizontal plane. In some embodiments, multiple wells can be formed into a pressed powder cake that can be symmetrically distributed with respect to a geometric center of the pressed powder cake. For example, the wells can be distributed in a pattern matching the shape of the powder cake about a geometric center of the powder cake. Thus, for example, a circular or oval powder cake can have a plurality of wells distributed in a circular or oval path about a geometric center of the surface of the pressed powder cake. Similarly, square or rectangular pressed powder cakes can similarly be provided with a plurality of wells of any desired shaped so distributed about the geometric center of the top surface of the pressed powder cake. The wells can be any desired suitable size.

Similarly, square shaped depressions can be configured with a width or length ratio that is about five to about ninety five percent of the overall width or length of the square pan in increments of about one percent, and rectangular shaped depressions can be configured with a width or length ratio that is about five to about ninety five percent of the overall width or length of the rectangular pan in increments of about one percent.

Pressed cosmetic powders are typically a mix of various free flowing small particle size solids which in combination with liquids are blended and compressed into a compact form. Typical pressed powder formulations include the following functional materials, such as fillers (e.g., talc, mica, and sericite), compression aids (e.g., zinc, magnesium and stearate), texture enhancers that may include ceramic materials or tribological particles (e.g., lauroyl lysine, boron nitride, PTFE), colorants (e.g., iron oxides, titanium dioxide, ultramarines, chromium oxides), organic lakes, liquid binders (e.g., oils, esters, silicones) and preservatives (e.g., parabens, sodium benzoate).

The shape of the powder materials varies, and may be platelets to spherical with an average length or diameter anywhere from 0.1-2 microns (e.g., talc & silica) to greater than 150 microns (pearls & glitters). Typical eyeshadow formula compositions can include:

|  | % w/w |
| --- | --- |
| Fillers | 30.0-80.0 |
| Compression Aid | 2.0-5.0 |
| Texture Enhancers | 3.0-30.0 |
| Colorants | 2.0-25.0 |
| Pearlescents | 0.0-50.0 |
| Binders | 3.0-10.0 |
| Preservatives | 0.5-1.0 |
| Additional Ingredients | qs |

The pressed cosmetic powder cake mix is typically compressed into a metal pan, such a tin or aluminum pans, using hydraulic presses with steel "punches" or dies. The pressures necessary are formula dependent and typically vary from about 5 bars to 110 bars (in suitable increments, such as of about one bar) with dwell times from about 1 second to about 4 seconds. The powder cake may be compressed once or twice, as desired. The established pressure parameters are selected to ensure the integrity and performance of the final product. The height of the powder case in the pan varies from about 2 mm to about 12 mm, preferably from about 2 mm to about 6 mm.

The pressed cosmetic powder cake is specially designed such that the depression or well formed into the powder cake acts as a reservoir to contain liquid or liquid-like material (e.g., gel). The liquid in the depression is mixed with the powder cake with a manual applicator to allow an individual to easily apply a wet mixed powder onto their skin. The depression is preferably formed in such a way that it not only provides a unique aesthetic design, but also serves as an artistic tool to which droplets of water are added to the powder to be used not only as a dry powder but in wet form as well.

It is to be understood that the foregoing general description and the following detailed description are exemplary and are intended to provide further explanation of the disclosed embodiments. The accompanying drawings, which are incorporated in and constitute part of this specification, are included to illustrate and provide a further understanding of the disclosed methods and systems. Together with the description, the drawings serve to explain principles of the disclosure.

DETAILED DESCRIPTION OF THE DISCLOSED EMBODIMENTS

Figure 1:
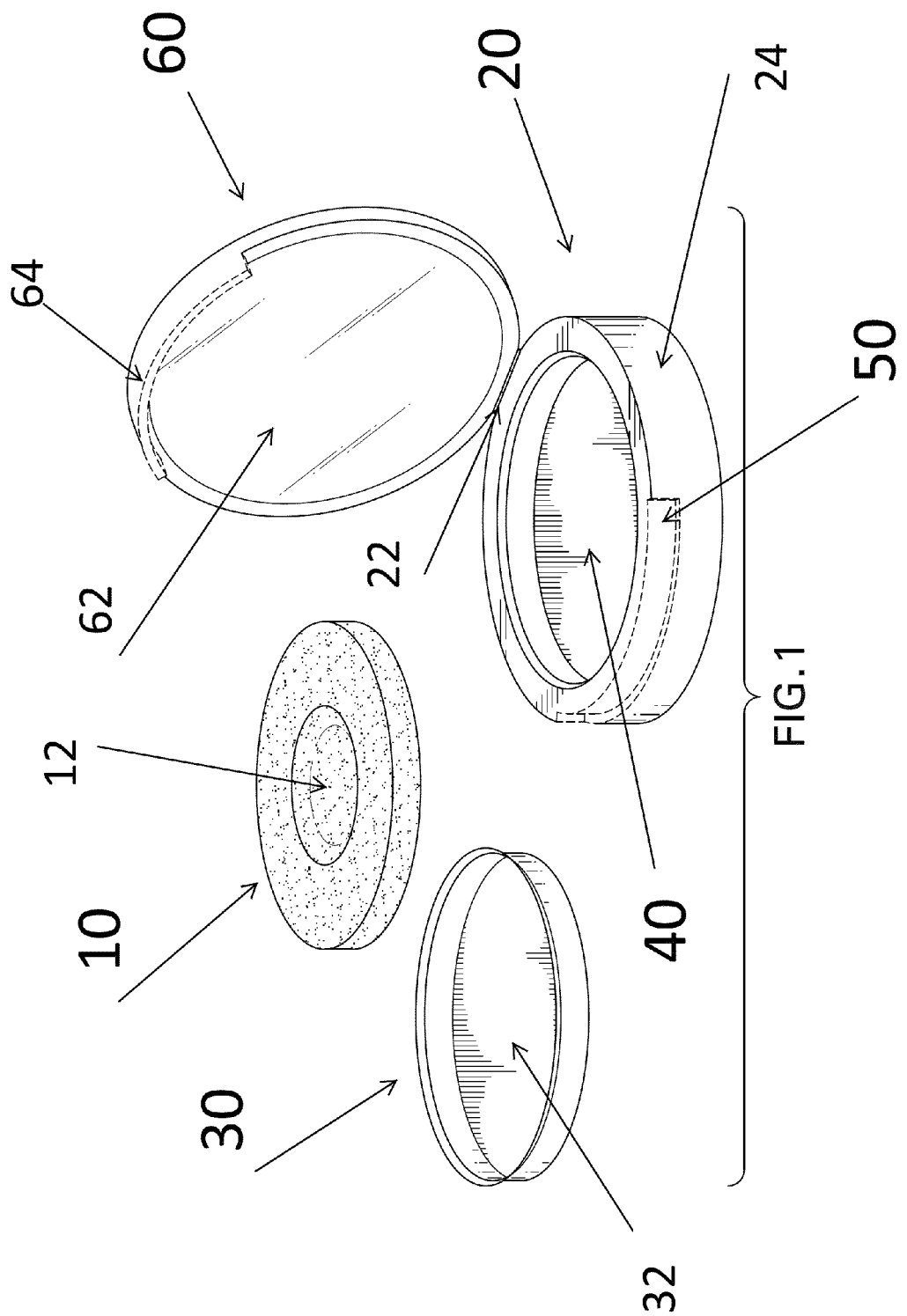
FIG. 1 is a perspective view of an exemplary pressed cosmetic powder cake, powder cake pan and cosmetic case in a round shape.

Referring now to the drawings in detail wherein like numerals indicate like elements throughout the several views, FIG. 1 illustrates an exemplary cosmetic product provided in accordance with the disclosure. As illustrated, the cosmetic product includes a pressed cosmetic powder cake to. The pressed cosmetic powder cake to defines therein a depression or well 12 in the center of the cake to for receiving a liquid. In FIG. 1, the depression 12 is in the shape of a circle. The cosmetic product includes a pan 30. The pan 30 defines therein a recess 32 to receive the powder cake to. The cosmetic product also includes a cosmetic case 20. The case includes a lower body portion or base 24 and an upper body portion or lid 60 coupled at a hinge 22, although it will be appreciated that embodiments can be provided with a separable lid and base. The hinge 22 allows the cosmetic case 20 to open and close. The lower body portion or base 24 is configured with an interior cavity 40 that receives the pan 30, which may be held in place, for example, by adhesive or a magnet, if the pan is made from steel. As illustrated, the lower body portion or base 24 is configured with a receiving groove 50 which is formed integrally in the inner circumference of the lower body portion or base 24. The upper body portion or lid 60 is configured with an inner side 62 for receiving a mirror. As illustrated, the upper body portion or lid is configured with an outwardly protruding sealing member 64 formed integrally on the outer circumference of the upper body portion or lid. The receiving groove 50, as illustrated, is configured to receive the outwardly protruding sealing member 64 allowing for the cosmetic case 20 be in a closed position.

The cosmetic case 20 may be made from a variety of materials, including plastic or metal, for example. The inner side 62 of the upper body portion or lid 60 may contain a mirror that is convex, concave or planar, as desired. In another embodiment, the inner side 62 of the upper body portion or lid 60 may also receive a powder puff. In another embodiment, the interior or exterior of the cosmetic case may receive an applicator, brush or a mixing tool. In another embodiment, the cosmetic case 20 may be made with an alternative structure for securing the upper body portion or lid 60 to the lower body portion or base 24 such as a clasp, magnet or other fastening means.

Figure 2:
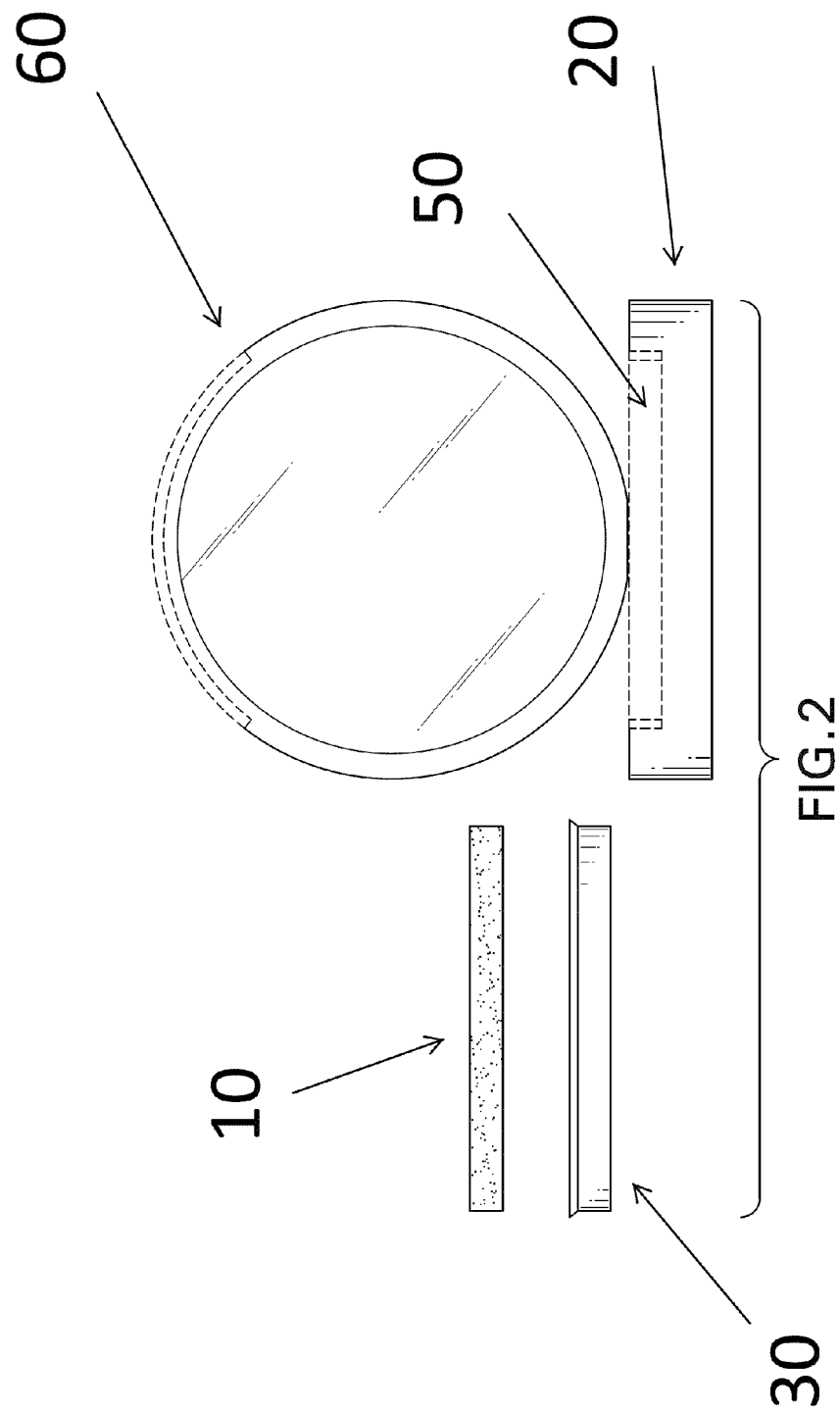
FIG. 2 is a front perspective side view thereof.
Figure 3:
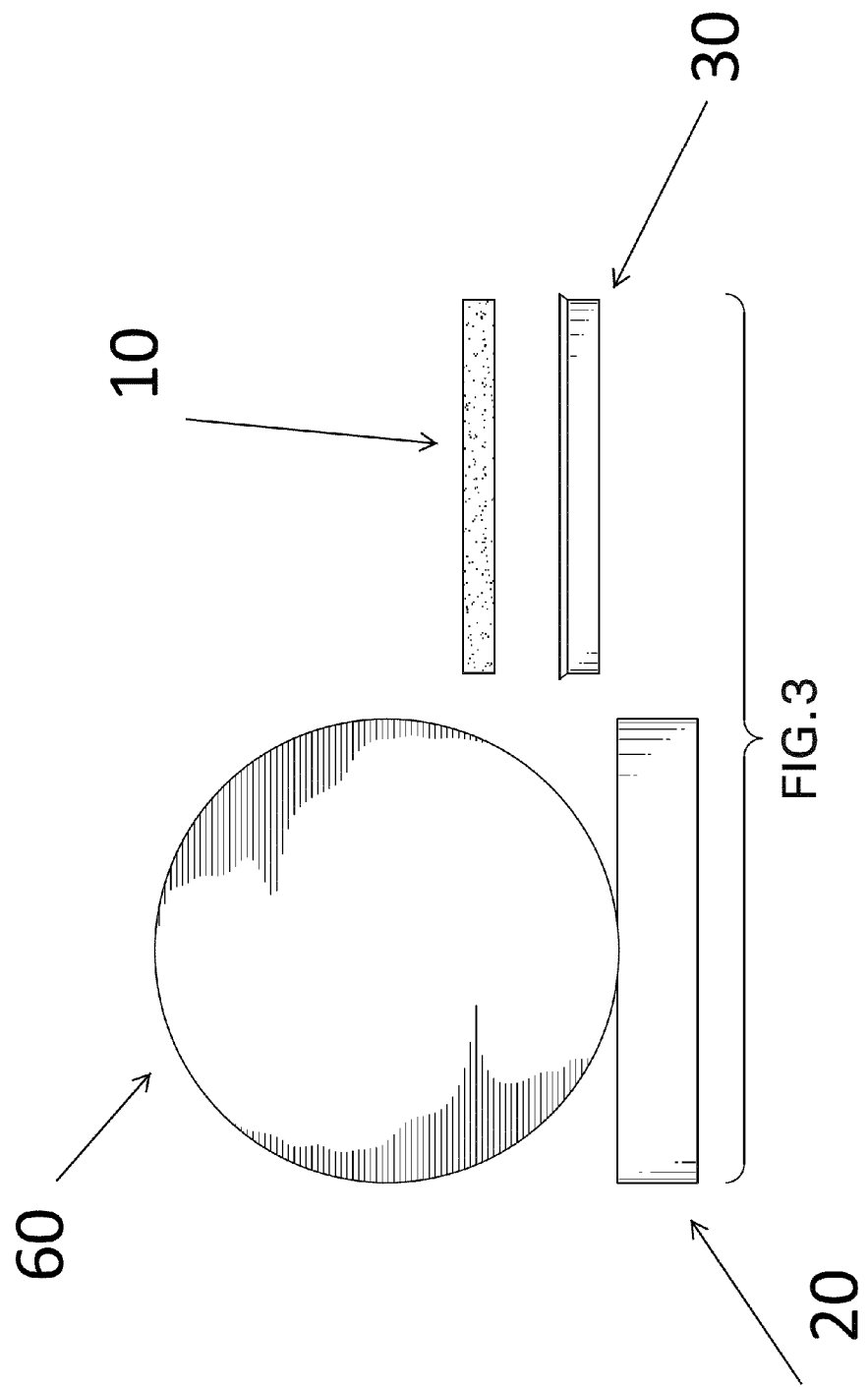
FIG. 3 is a front perspective side view, rotated 180 degrees thereof.
Figure 4:
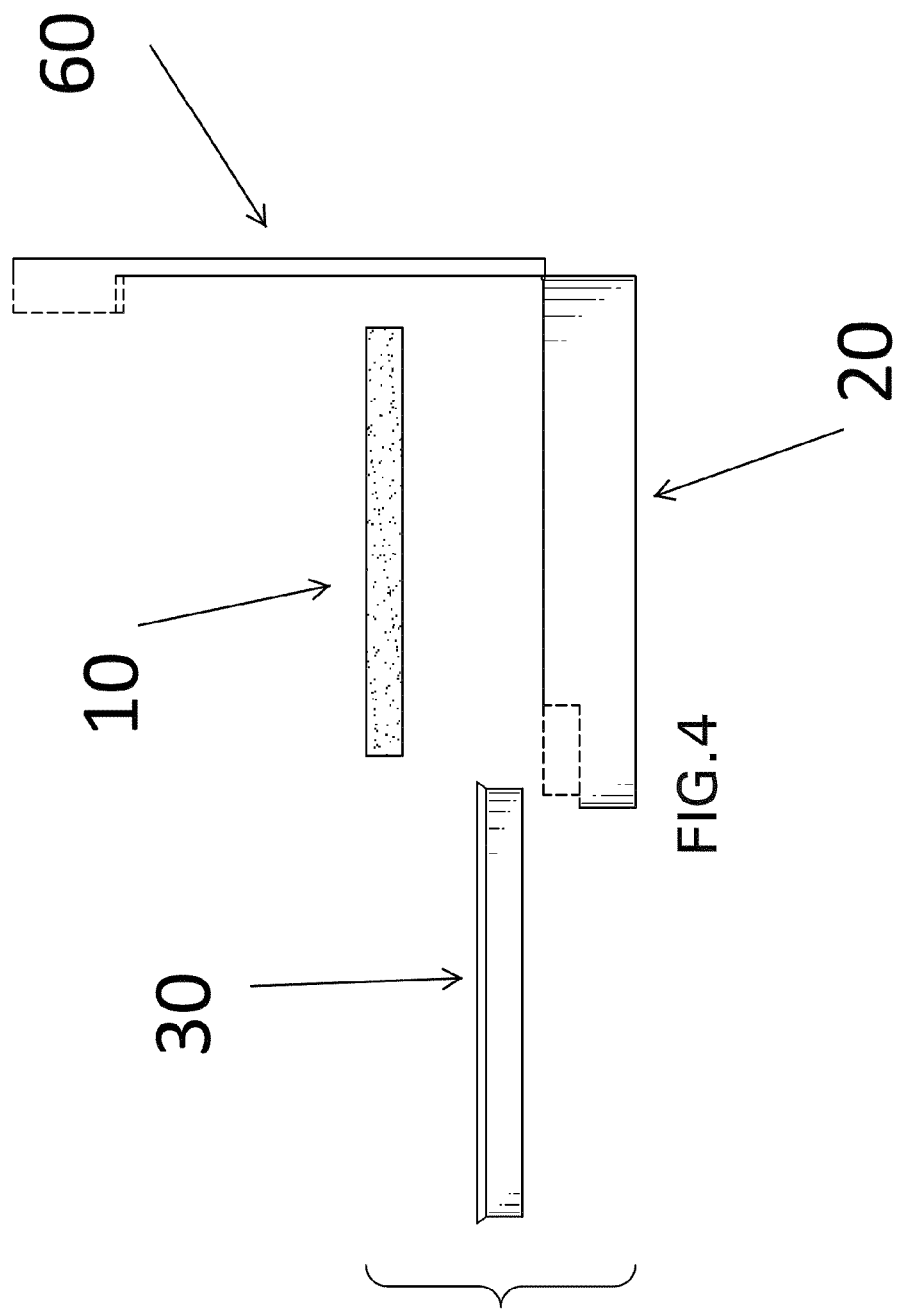
FIG. 4 is a front perspective side view of the embodiment of FIG. 1 showing the pan receiving the pressed cosmetic powder cake and pan.
Figure 5:
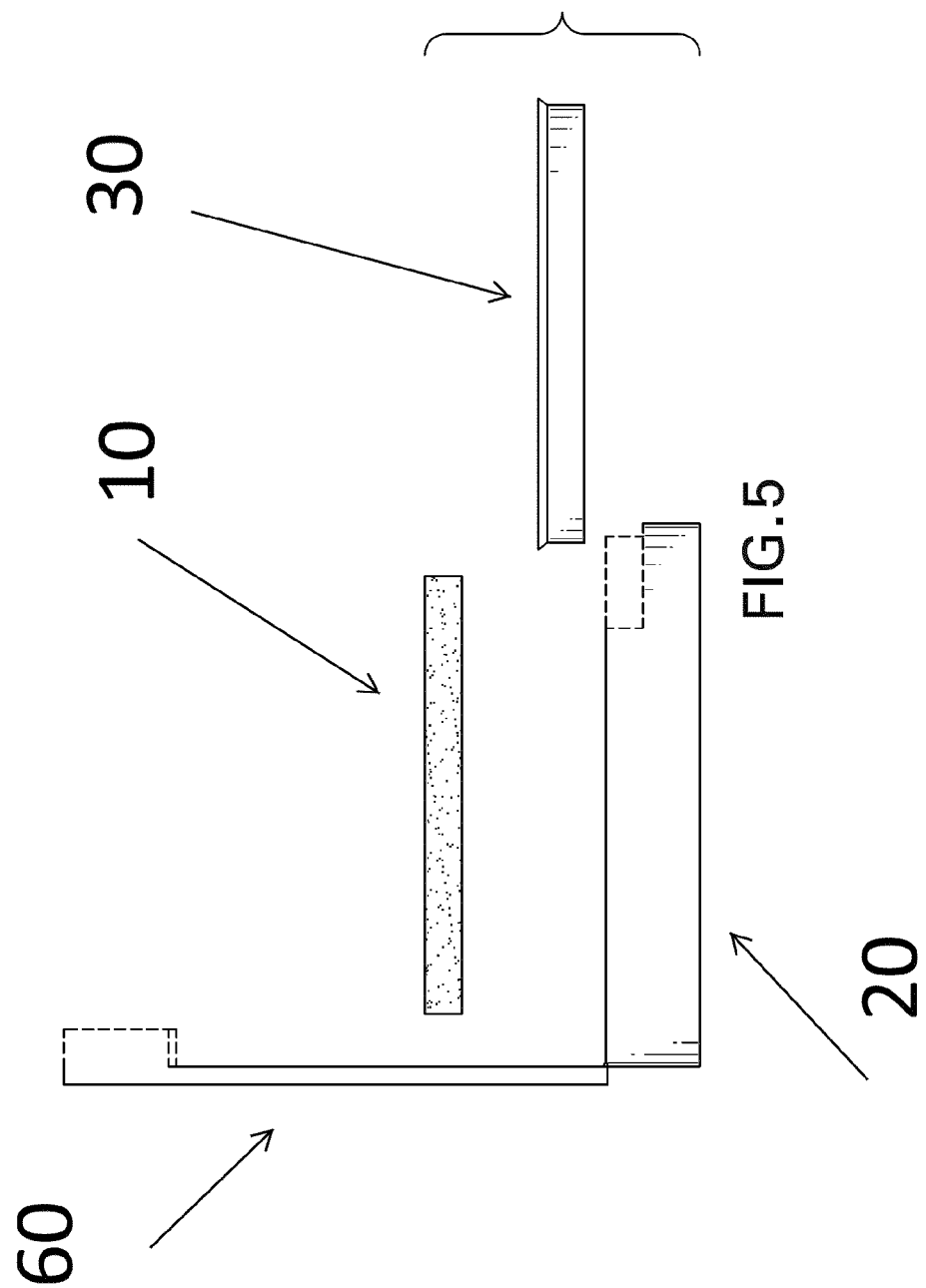
FIG. 5 a front perspective side view of the embodiment of FIG. 4, rotated 180 degrees.
Figure 6:
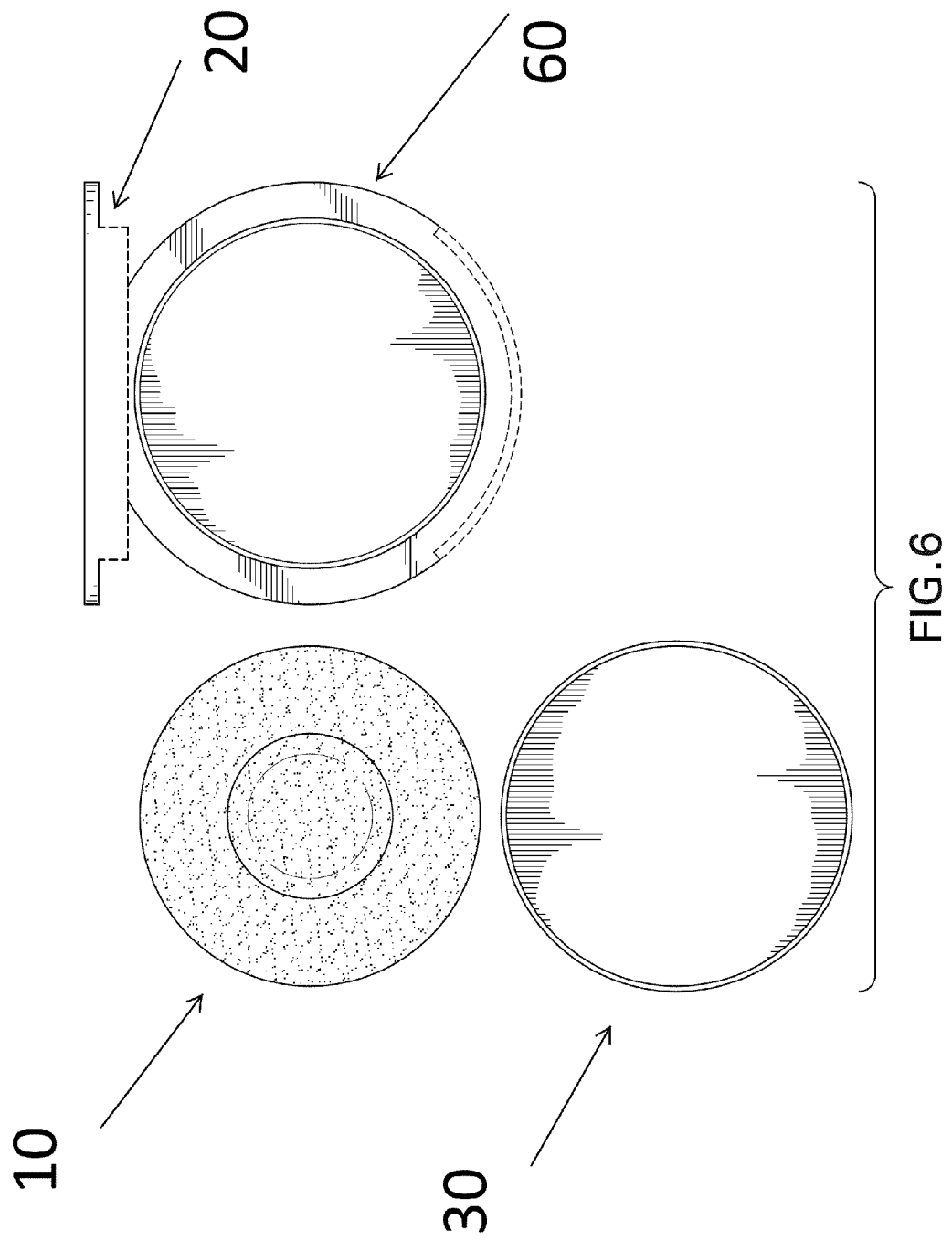
FIG. 6 is a top perspective view of the embodiment of FIG. 4.
Figure 7:
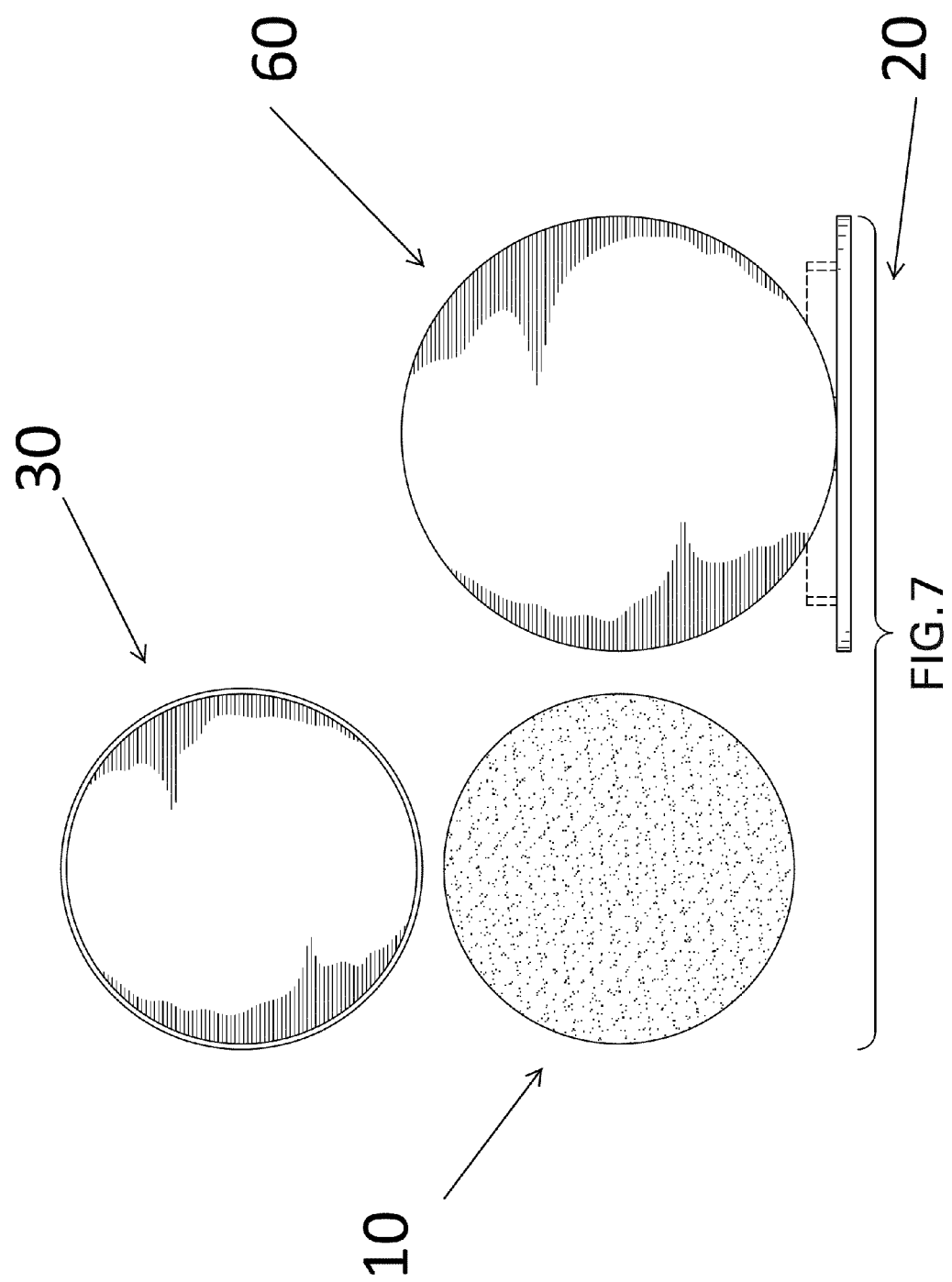
FIG. 7 is a bottom perspective view of the embodiment of FIG. 4.

FIG. 2 shows a front perspective side view of the cosmetic product components. FIG. 3 shows a front perspective side view, rotated 180 degrees where the back side of the cosmetic products components are shown. FIG. 4 shows a front perspective side view of the cosmetic case 20 receiving the pressed cosmetic powder cake 10 and pan 30. Similarly, FIG. 5 shows a front perspective side view of the cosmetic case 20 receiving the pressed cosmetic powder cake 10 and pan 30, rotated 180 degrees. FIG. 6 shows a top perspective view of the cosmetic case 20 receiving the pressed cosmetic powder cake 10 and pan 30. Similarly, FIG. 7 is a bottom perspective view of the cosmetic case 20 receiving the pressed cosmetic powder cake 10 and pan 30.

Figure 8:
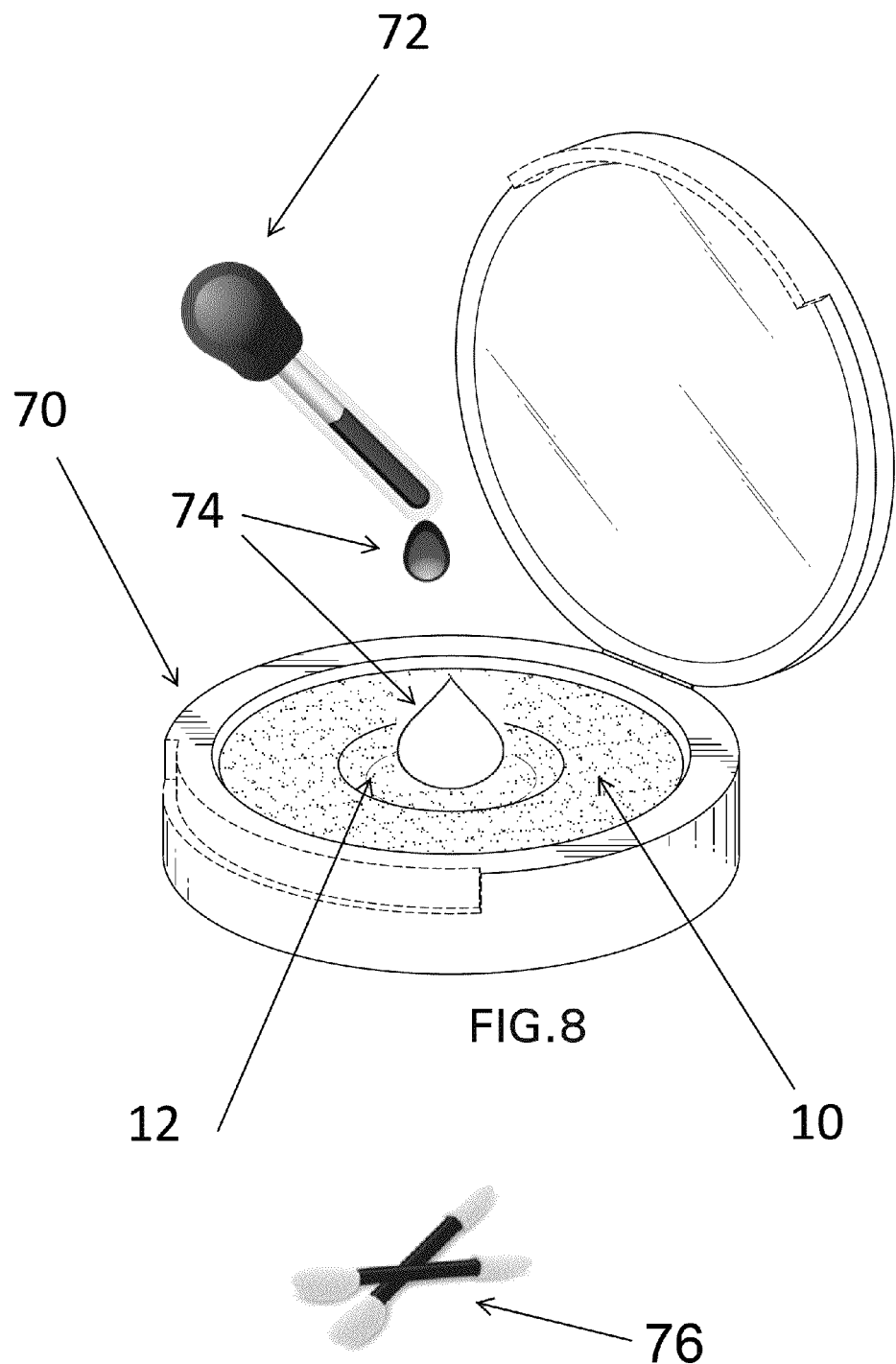
FIG. 8 is a perspective view of the fully assembled cosmetic product of FIG. 1 with a liquid applicator.
Figure 9:
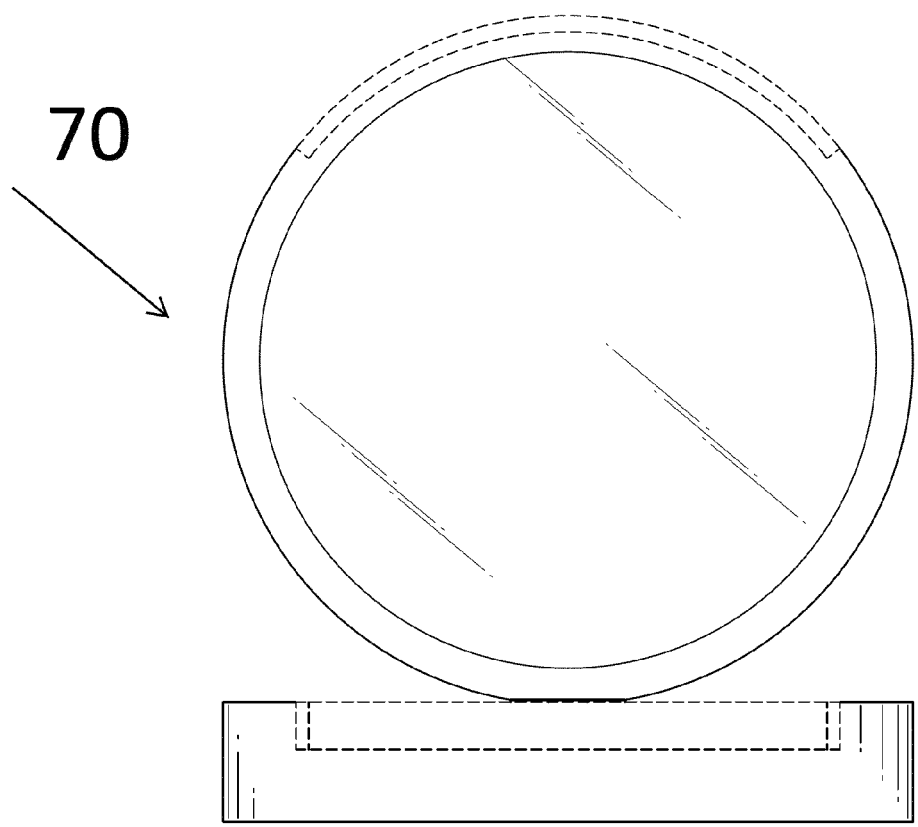
FIG. 9 is a front perspective view of the embodiment of FIG. 8 in a closed position.
Figure 10:
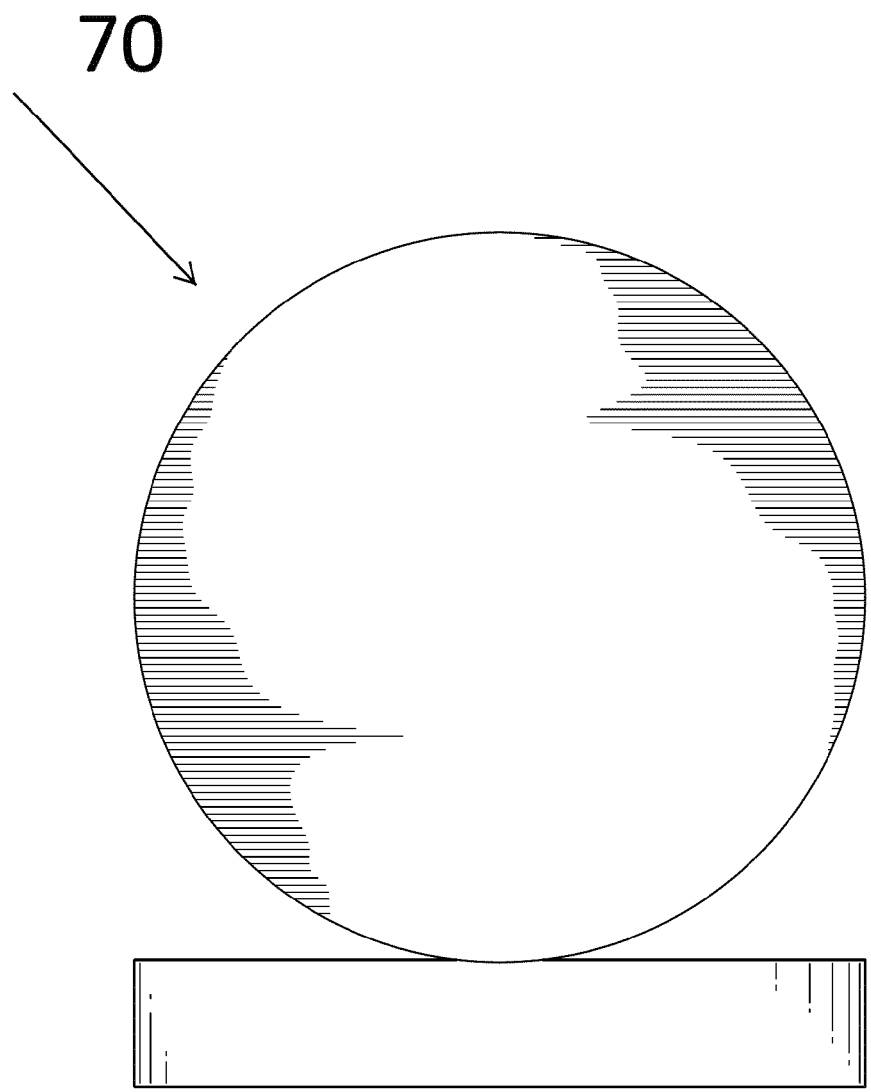
FIG. 10 is a bottom perspective view of the embodiment of FIG. 8 in a closed position.

FIG. 8 is a perspective view of the fully assembled cosmetic product 70 in a round shape. FIG. 8. also shows an applicator or pipette 72 containing a liquid, preferably water. The applicator 72 drops a liquid droplet 74 into the depression 12 of the pressed cosmetic powder cake to. A brush or a mixing tool 76 can then be used to combine the liquid droplet 74 with the pressed cosmetic powder cake to. The mixture can then be applied by the user. FIG. 9 shows a front perspective view of the fully inserted cosmetic product 70 in a closed position. FIG. 10 shows the bottom perspective view of the fully inserted cosmetic product 70 in a closed position.

Figure 11:
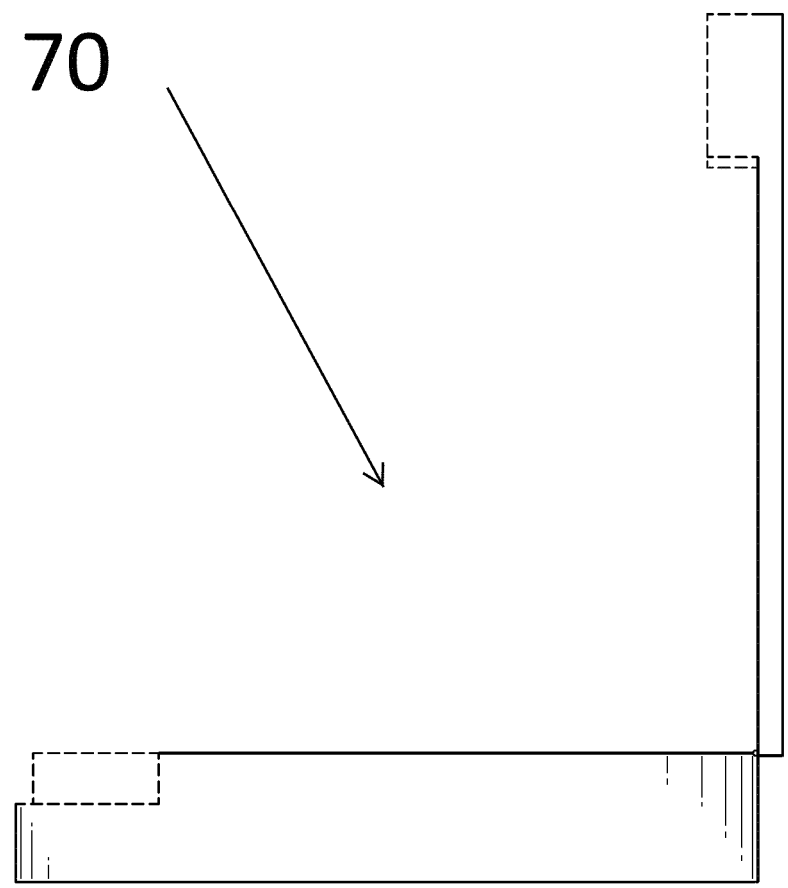
FIG. 11 is a front perspective side view of the embodiment of FIG. 8.
Figure 12:
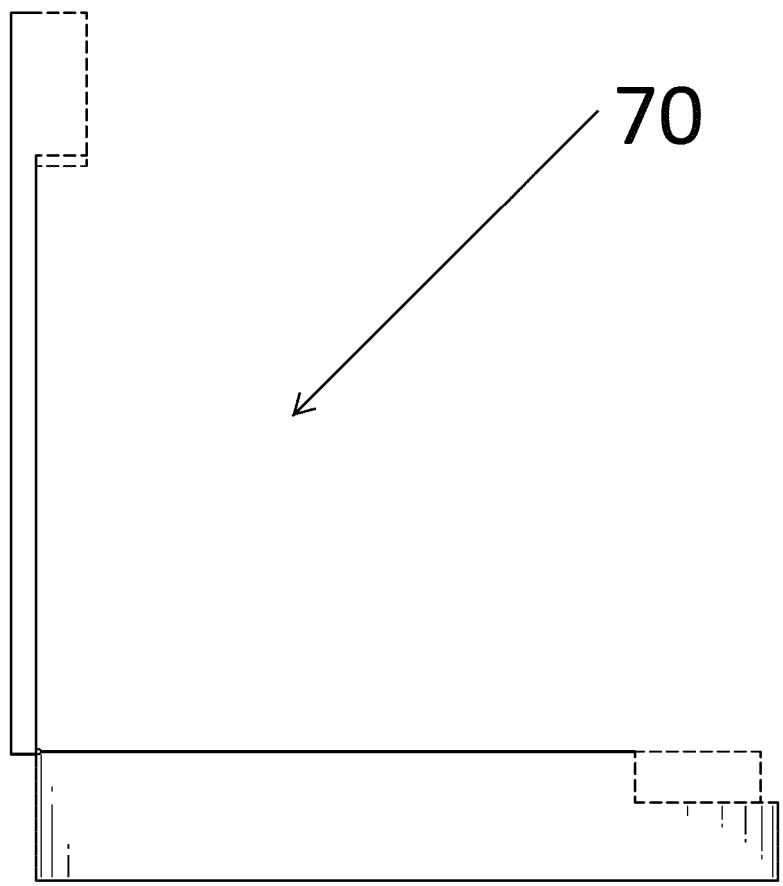
FIG. 12 is a front perspective side view of the embodiment of FIG. 8, rotated 180 degrees.
Figure 13:
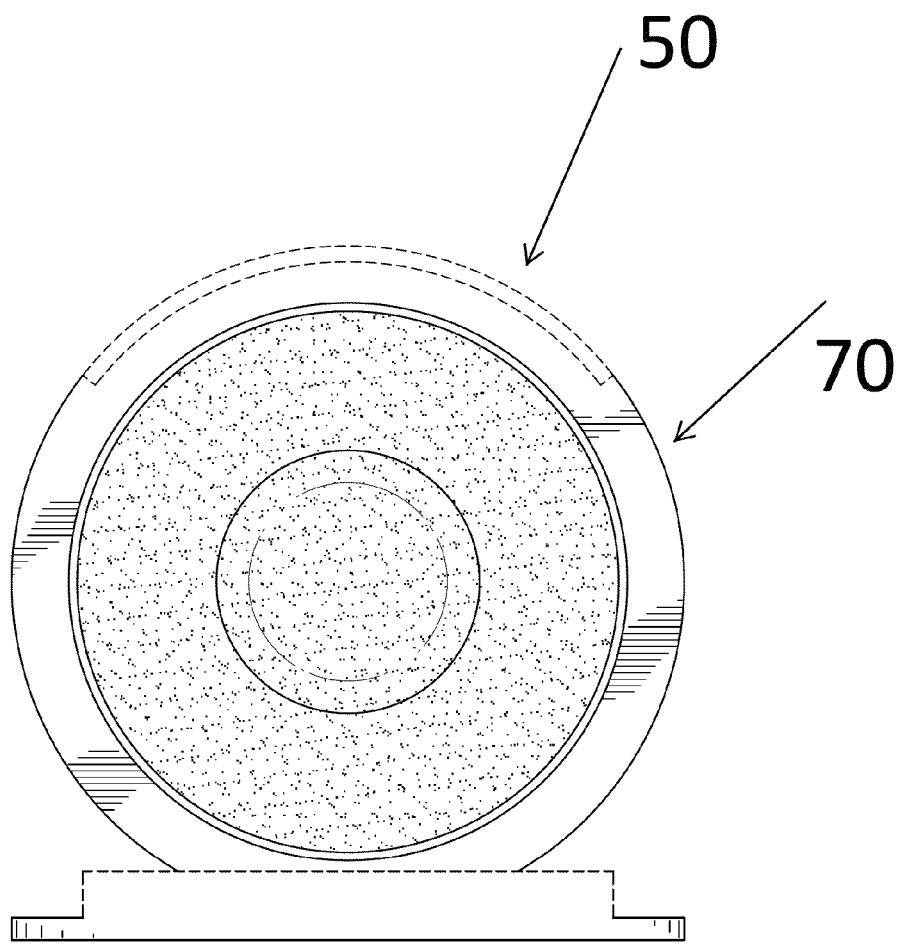
FIG. 13 is a top perspective view of the embodiment of FIG. 8.
Figure 14:
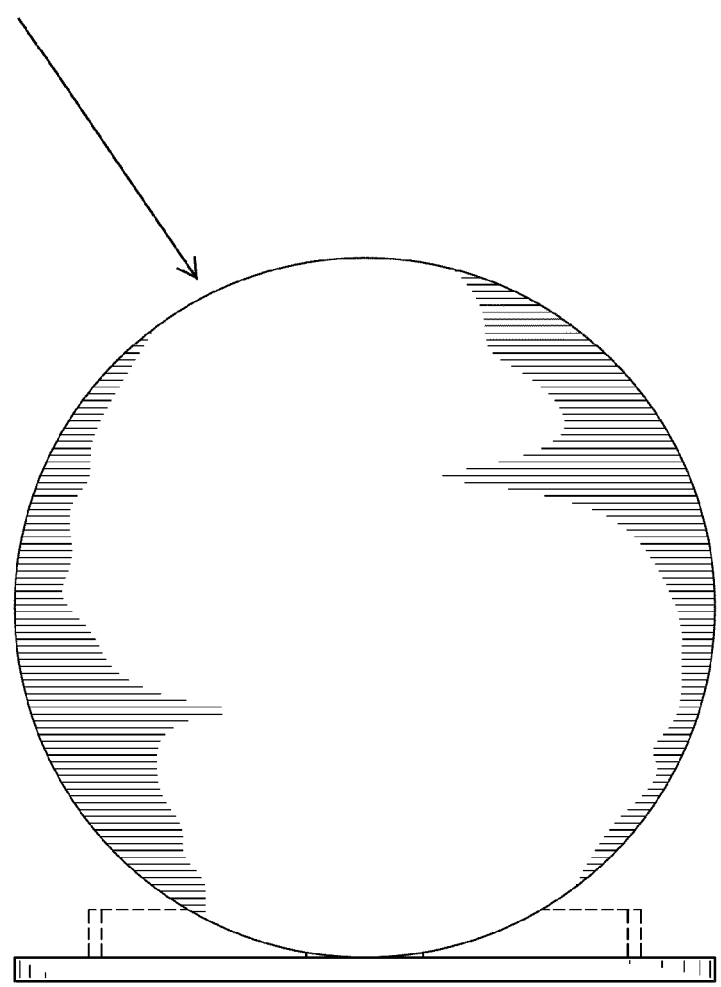
FIG. 14 is a bottom perspective view of the embodiment of FIG. 8.

FIG. 11 is a front perspective side view of the fully inserted cosmetic product 70 in an open position. Similarly, FIG. 12 is a front perspective side view of the fully inserted cosmetic product, rotated 180 degrees. In addition, FIG. 13 presents a top perspective view of the fully inserted cosmetic product 70 and FIG. 14 presents a bottom perspective view of the fully inserted cosmetic product 70.

Figure 15:
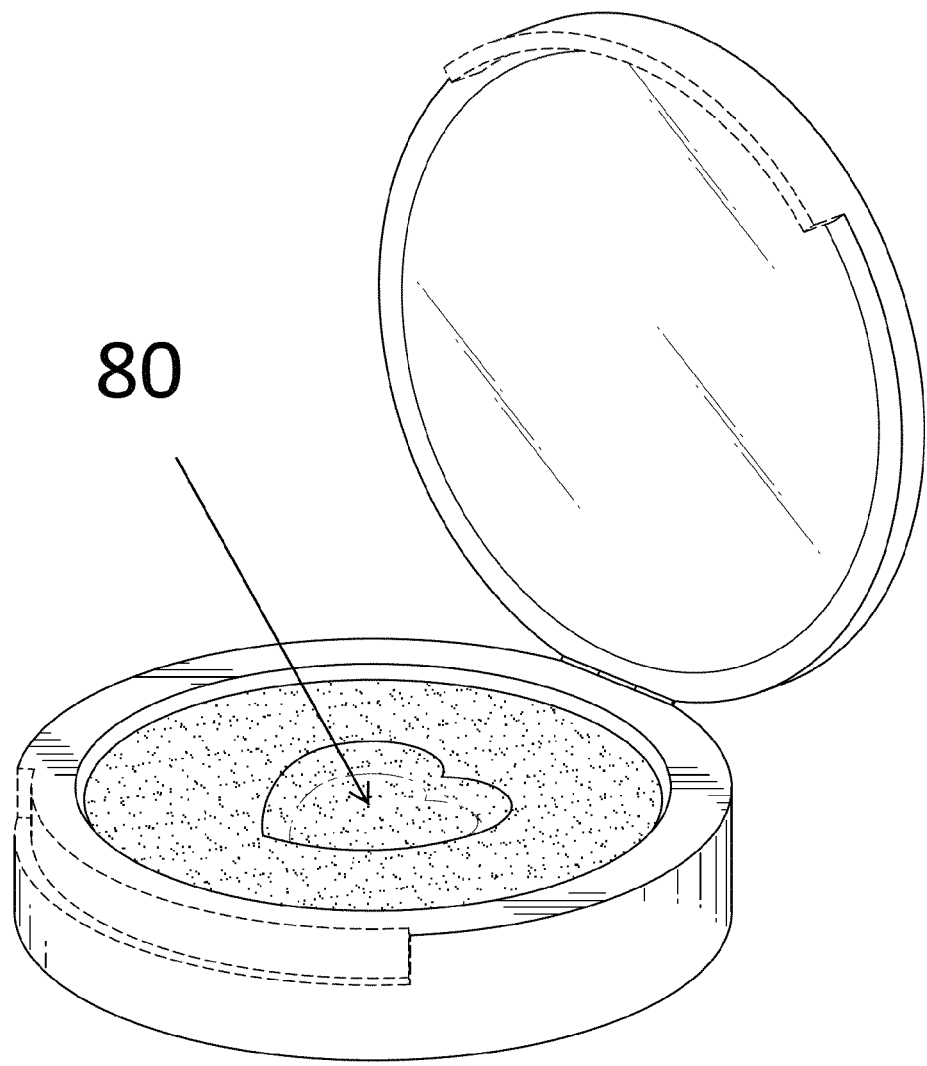
FIG. 15 is a perspective view of the embodiment of FIG. 8, showing the pressed cosmetic powder cake with a depression formed into the cake in the shape of a heart.
Figure 16:
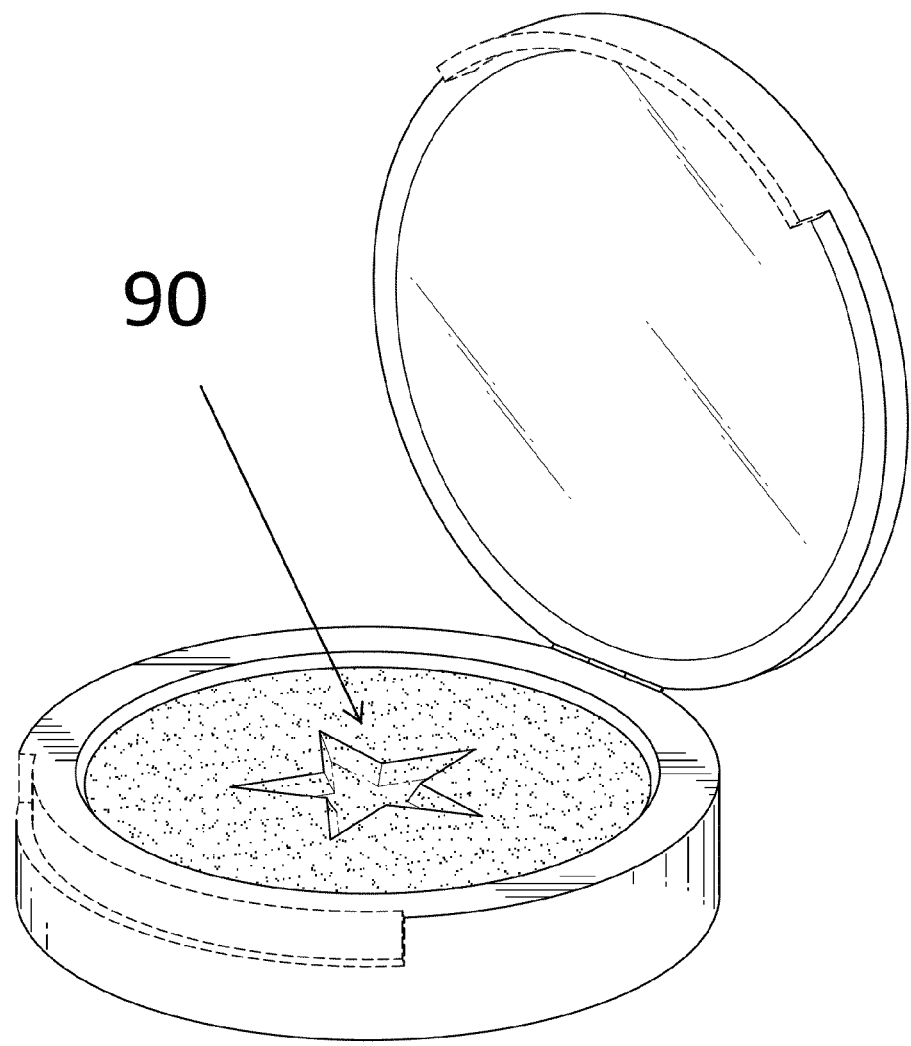
FIG. 16 is a perspective view of the embodiment of FIG. 8, showing the pressed cosmetic powder cake with a depression in the shape of a star.
Figure 17:
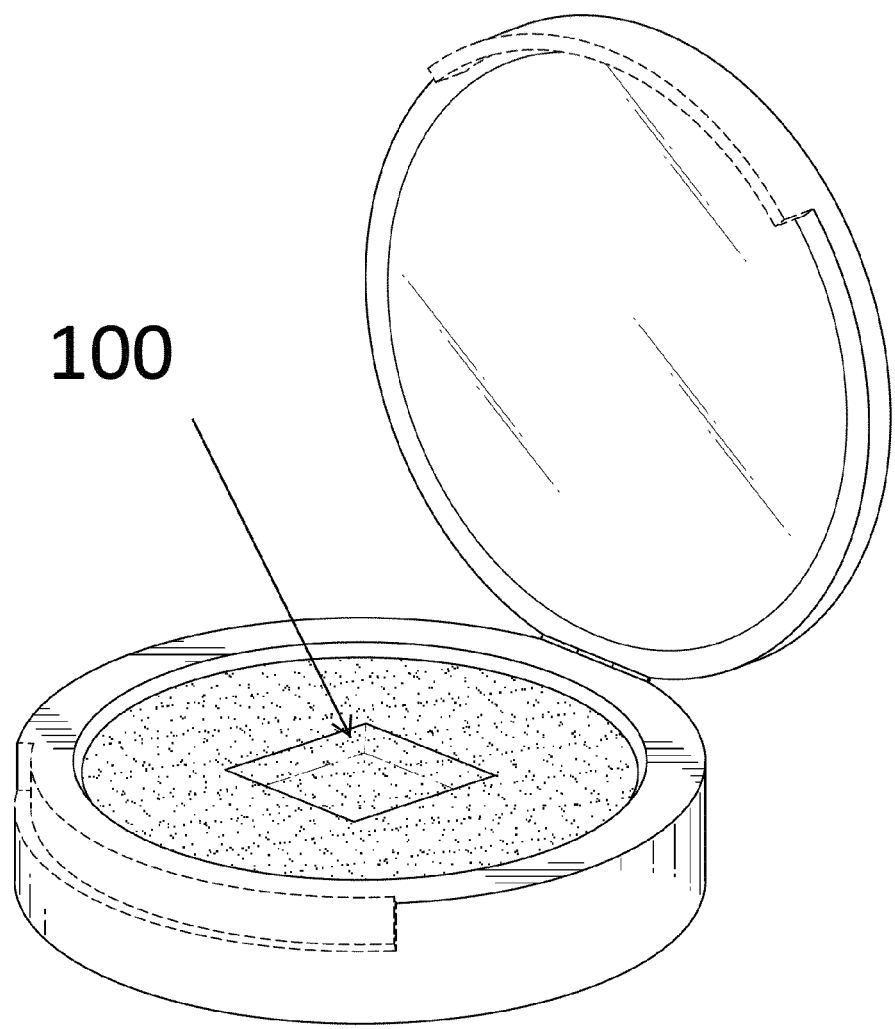
FIG. 17 is a perspective view of the fully inserted cosmetic product of FIG. 8, showing the pressed cosmetic powder cake with a depression in the shape of a square.
Figure 18:
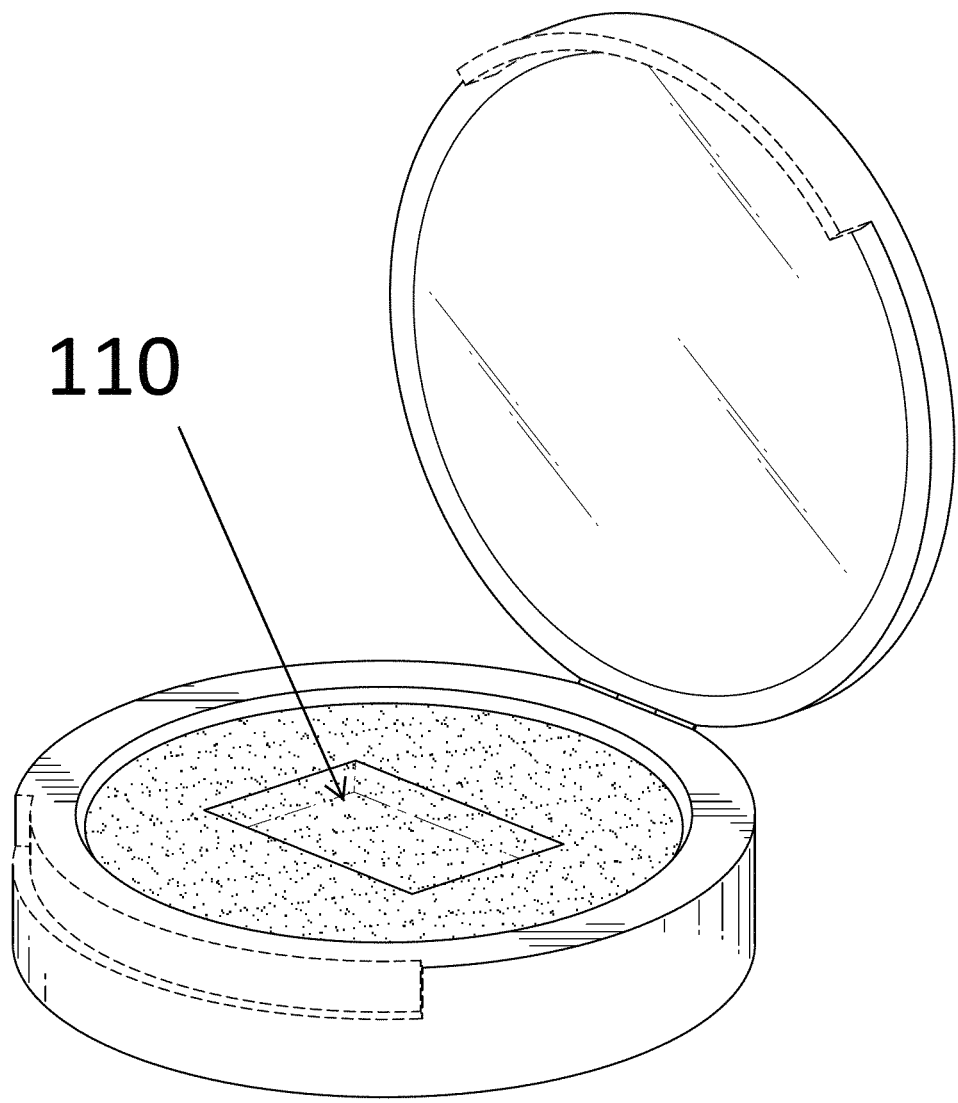
FIG. 18 is a perspective view of the fully inserted cosmetic product of FIG. 8, showing the pressed cosmetic powder cake with a depression in the shape of a rectangle.
Figure 19:
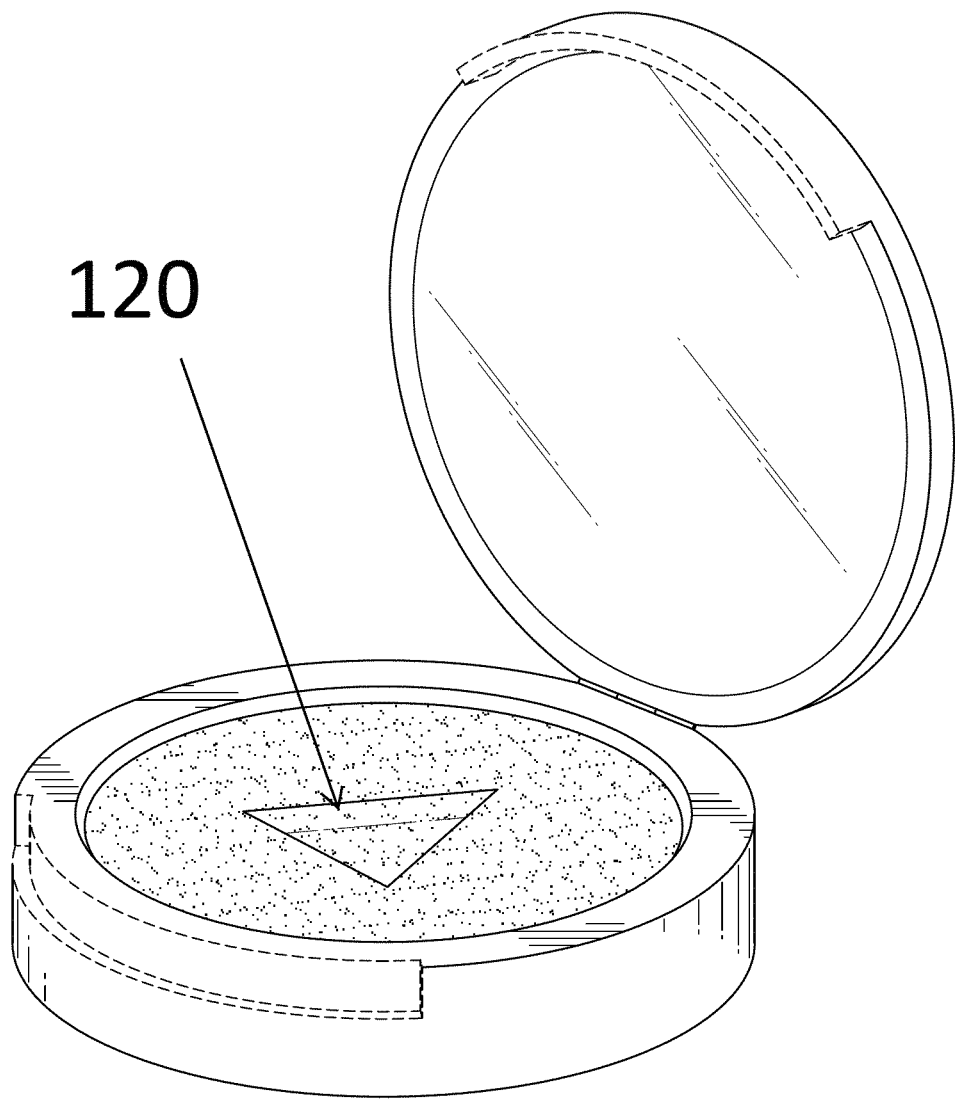
FIG. 19 is a perspective view of the fully assembled cosmetic product of FIG. 8, showing the pressed cosmetic powder cake with a depression in the shape of a triangle.

The pressed cosmetic powder cake to may contain depressions of a variety of shapes and sizes. FIG. 15 shows a pressed cosmetic powder cake to having a depression in the shape of a heart 80. FIG. 16 shows a pressed cosmetic powder cake to having a depression in the shape of a star 90. FIG. 17 shows a pressed cosmetic powder cake 10 having a depression in the shape of a square 100. FIG. 18 shows a pressed cosmetic powder cake 10 having a depression in the shape of a rectangle 110. FIG. 19 shows a pressed cosmetic powder cake to having a depression in the shape of a triangle 120. The depression in the powder cake is preferably made prior to packaging during the manufacturing stage. The formation of the depression in the upper face of the powder cake is preferably automated and allows for a variety of shapes and sizes to be designed that are not shown, including, but not limited to, diamonds, alphabetical initials, numbers and objects such as animals or other natural forms, such as seashells, waterfalls, trees, and the like.

The depth of the well or depression in the various embodiments described herein is preferably deep enough to prevent a water or other liquid or gel from rolling off of the hydrophobic surface of the powder cake. For example, the depth of the well or depression can be from about 0.5 mm to about 1.0 mm depending on the thickness or depth of the pressed powder cake, such as from about 1.0 mm to about 5.0 mm, about 2.0 mm to 3.0 mm, about 1 mm, about 1.5 mm, about 2 mm, about 2.5 mm, about 3 mm, about 3.5 mm, about 4 mm, about 4.5 mm, about 5 mm, about 5.5 mm, about 6 mm, about 6.5 mm, about 7 mm, about 7.5 mm, about 8 mm, about 8.5 mm, about 9 mm, about 9.5 mm, and about 10 mm.

By way of further example, the depth of the well or depression can be from about 10% to about 90% of the depth (height) of the pressed powder cake, such as from about 20% to about 70%, about 30% to about 60%, about 10%, about 15%, about 20%, about 25%, about 30%, about 35%, about 40%, about 45%, about 50%, about 55%, about 60%, about 65%, about 70%, about 75%, about 80%, about 85% and about 90% of the depth (height) of the pressed powder cake.

Figure 20:
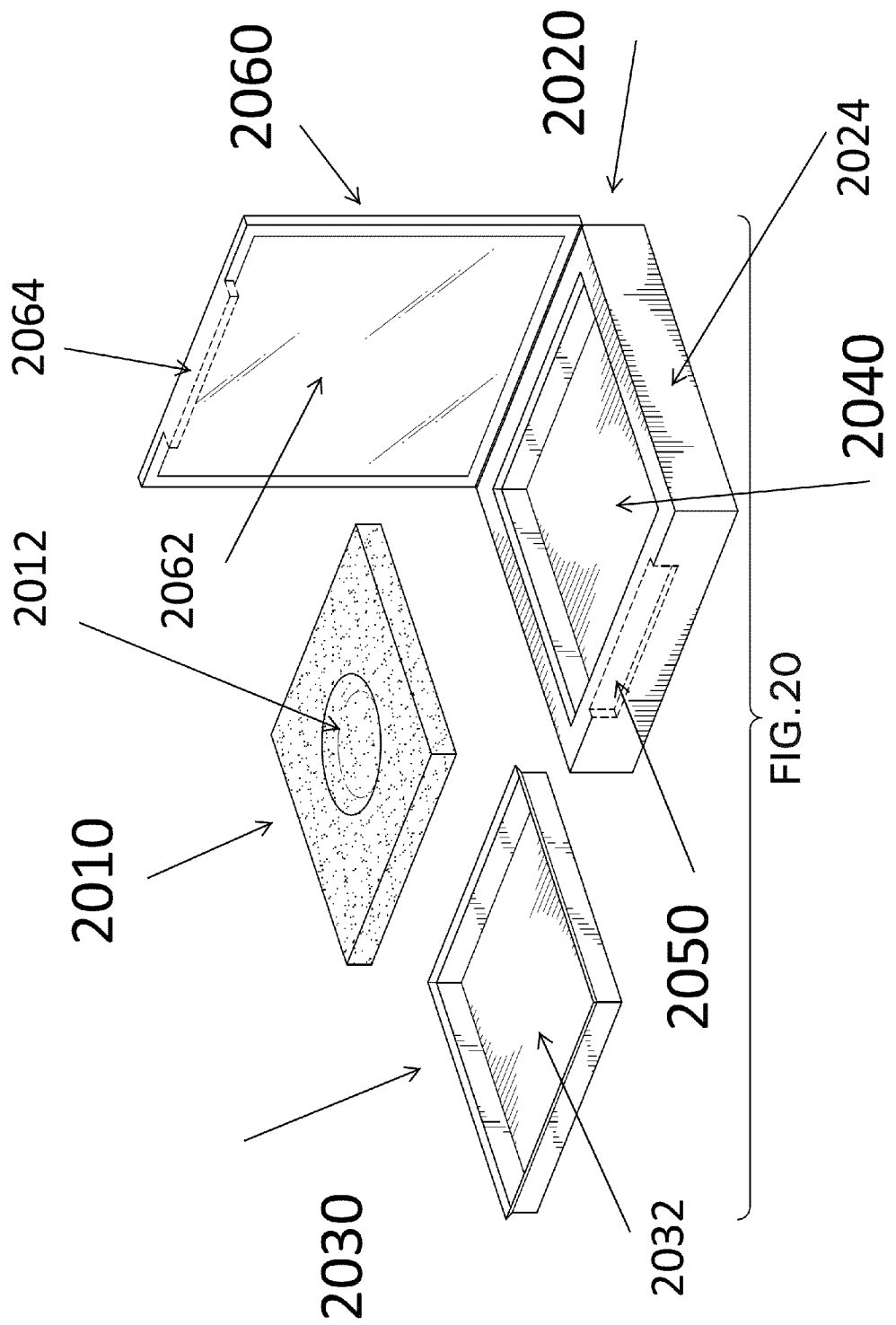
FIG. 20 is a perspective view of the pressed cosmetic powder cake, pan and cosmetic case in a square shape.

The components of the cosmetic product may be made in a variety of shapes and sizes. In another embodiment, as shown in FIG. 20, the components of the cosmetic product are all square shaped. FIG. 20 shows a pressed cosmetic powder cake 2010. The pressed cosmetic powder cake 10 contains a depression 2012 in the center of the cake 2010 for receiving a liquid. The depression in FIG. 20 is round but as described above, the depressions can also be made in a variety of sizes and shapes while still allowing for the components of the cosmetic product to be in square shaped, such as those illustrated in U.S. Design application Ser. No. 29/468,950 filed Oct. 4, 2013.

Figure 21:
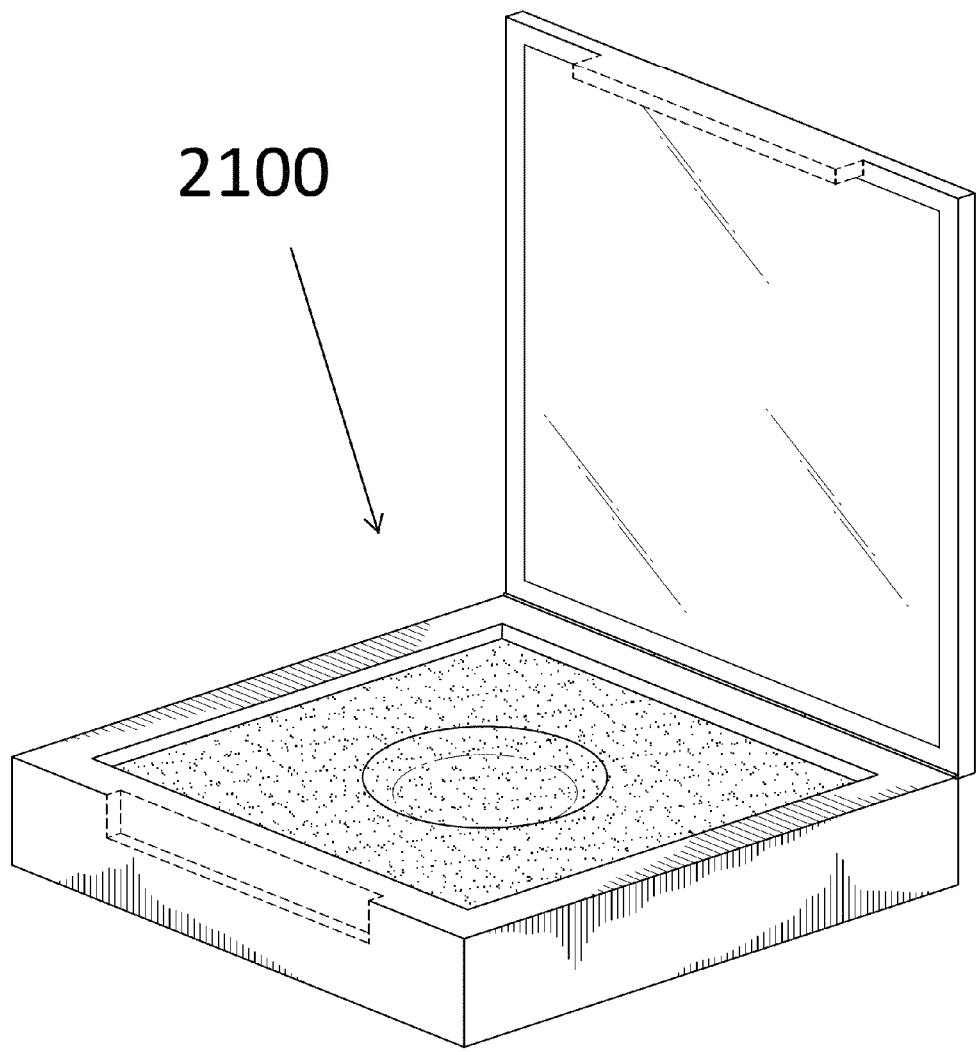
FIG. 21 is a perspective view of the fully assembled cosmetic product of FIG. 20.

FIG. 20 also shows the a square shaped pan 2030. The pan 2030 defines a recess 2032 therein to receive the powder cake 2010. FIG. 20 also illustrates the cosmetic case 2020. The case includes a lower body portion or base 2024 and an upper body portion or lid 2060 coupled at a hinge (not shown). The lower body portion or base 2024 is defines therein an interior cavity 2040 that receives the pan 2030. The lower body portion or base 2024 is configured with a receiving groove 2050 which is formed integrally in the inner circumference of the lower body portion or base 2024. The upper body portion or lid 2060 is configured with an inner side 2062 for receiving a mirror. The upper body portion or lid is configured with an outwardly protruding sealing member 2064 formed integrally on the outer circumference of the upper body portion or lid. The receiving groove 2050 is configured to receive the outwardly protruding sealing member 2064 allowing for the cosmetic case 2020 be in a closed position. FIG. 21 shows the square shaped cosmetic product components fully inserted.

Figure 22:
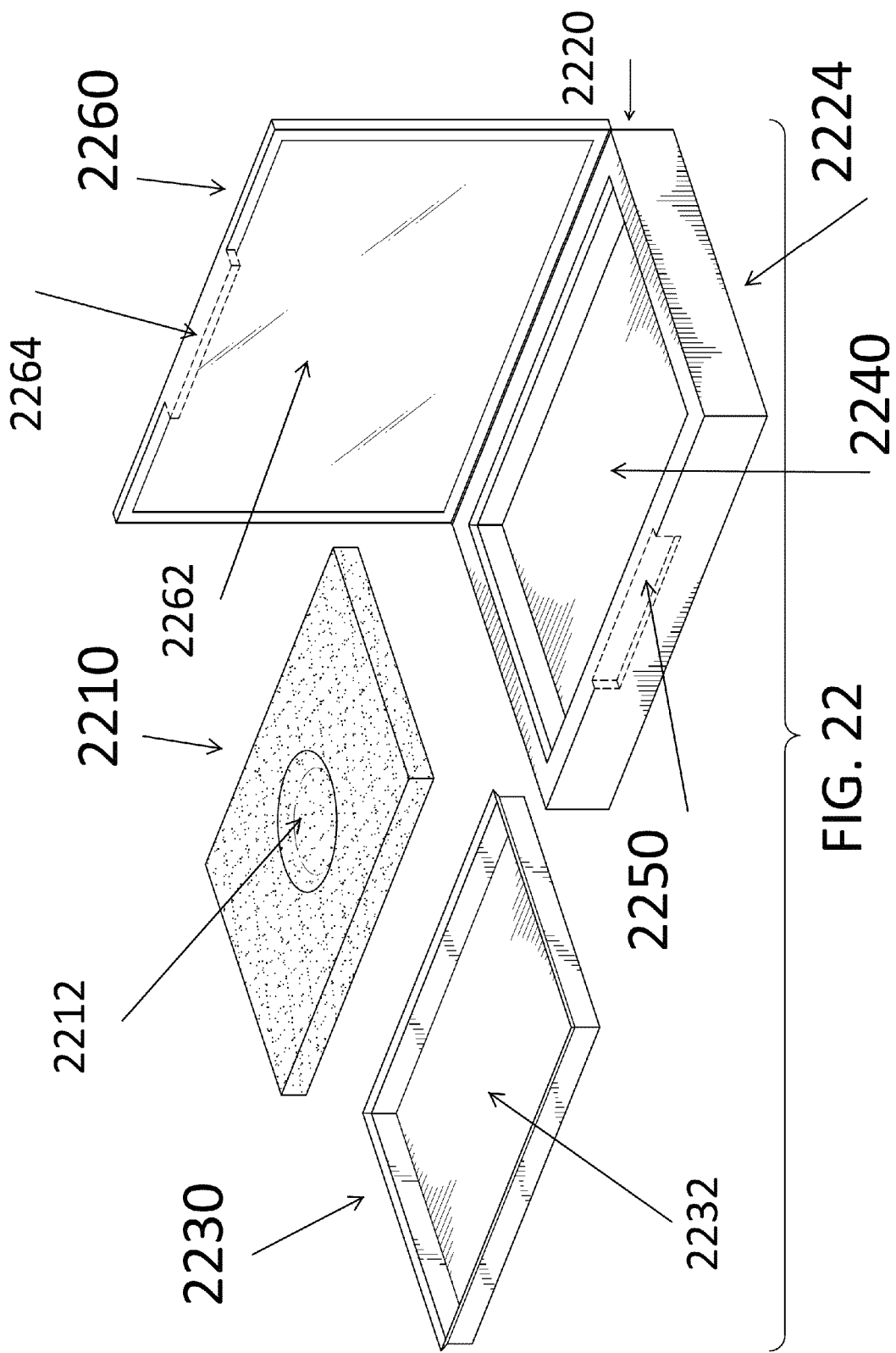
FIG. 22 is a perspective view of the pressed cosmetic powder cake, pan and cosmetic case in a rectangle shape.
Figure 23:
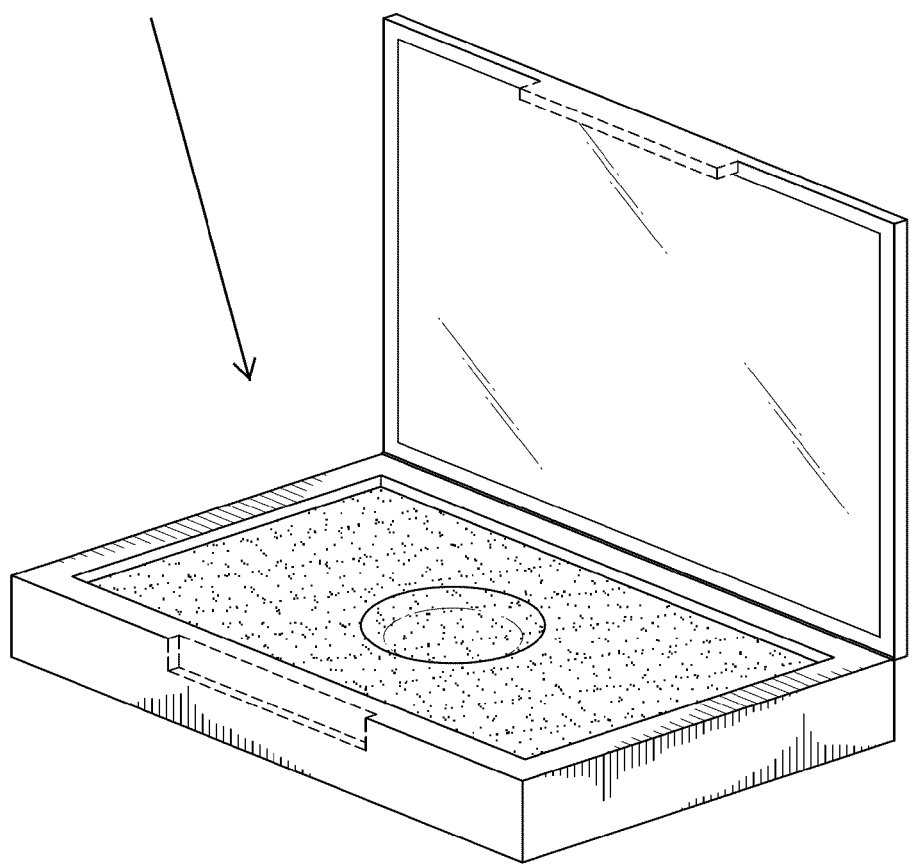
FIG. 23 is a perspective view of the fully assembled cosmetic product of FIG. 22.

In another embodiment, as shown in FIG. 22, the components of the cosmetic product are all in a rectangular shape. FIG. 22 shows a pressed cosmetic powder cake 2210. The pressed cosmetic powder cake 2210 defines a depression or well 2212 in the center of the cake 2210 for receiving a liquid (or gel). The depression in FIG. 22 is round but as described above, the depressions can also be made in a variety of sizes and shapes while still allowing for the components of the cosmetic product to be in rectangular shape. FIG. 22 also shows the a square shaped pan 2230. The pan 2230 contains a recess 2232 to receive the powder cake 2210. FIG. 22 also shows the cosmetic case 2220. The case includes a lower body portion or base 2224 and an upper body portion or lid 2260 coupled at a hinge (not shown). The lower body portion or base 2224 is configured with an interior cavity 2240 that receives the pan 2230. The lower body portion or base 2224 is configured with a receiving groove 2250 which is formed integrally in the inner circumference of the lower body portion or base 2224. The upper body portion or lid 2260 is configured with an inner side 2262 for receiving a mirror. The upper body portion or lid is configured with an outwardly protruding sealing member 2264 formed integrally on the outer circumference of the upper body portion or lid. The receiving groove 2250 is configured to receive the outwardly protruding sealing member 2264 allowing for the cosmetic case 2220 be in a closed position. FIG. 23 shows the rectangular shaped cosmetic product components fully inserted.

The present disclosure discloses improved methods for using a cosmetic product. The method of using the cosmetic product of the present disclosure, includes using an applicator to drop a liquid or gel, as desired into a depression or well pre-formed into a pressed cosmetic powder cake; mixing the liquid with the content of the pressed cosmetic powder cake with a mixing tool, and applying the mixed wet cosmetic product on a user's skin. The mixing tool can be the applicator or pipette used to drop liquid into the depression, a cotton swab, or other suitable applicator.

All statements herein reciting principles, aspects, and embodiments of the disclosure, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

In the disclosure hereof any element expressed as a means for performing a specified function is intended to encompass any way of performing that function. Applicants thus regard any means which can provide those functionalities as equivalent to those shown herein. It is intended that the present disclosure include modifications and variations that are within the scope of the subject disclosure and equivalents.

What is claimed is:

1. A cosmetic product, including:
   a pressed cosmetic powder cake composed of hydrophobic material being defined in part by a generally planar upper surface, the generally planar upper surface having a width that is substantially greater than the depth of the pressed powder cake; the generally planar upper surface of the pressed cosmetic powder cake defining a well therein for receiving a liquid or gel, the well being configured to retain the liquid or gel to prevent the liquid or gel from rolling off the pressed powder cake;
   a droplet of liquid or gel, deposited and maintained within the well of the pressed cosmetic powder cake, the liquid configured to mix with the pressed cosmetic powder cake for application by a user;
   a pan defining a recess therein for receiving the pressed cosmetic powder cake; and
   a cosmetic case; the cosmetic case including a base portion and a lid that can be coupled to the base portion, wherein the base portion defines an interior cavity for receiving the pan and pressed cosmetic powder cake.

2. The cosmetic product of claim 1, wherein the depth of the well defined in the pressed powder cake is between about 10% to about 90% of the depth of the pressed powder cake.

3. The cosmetic product of claim 1, wherein the depth of the well defined in the pressed powder cake is between about 20% to about 70% of the depth of the pressed powder cake.

4. The cosmetic product of claim 1, wherein the width of the well defined in the pressed powder cake is between about 5% to about 95% of the width of the pressed powder cake.

5. The cosmetic product of claim 1, wherein lid includes an inner side for receiving a mirror.

6. The cosmetic product of claim 1, wherein the pressed cosmetic powder cake, the well, the pan, and the cosmetic case are round.

7. The cosmetic product of claim 1, wherein the pressed cosmetic powder cake, the well, the pan, and the cosmetic case are square.

8. The cosmetic product of claim 1, wherein the pressed cosmetic powder cake, the well, the pan, and the cosmetic case are rectangular.

9. The cosmetic product of claim 1, wherein the base portion and lid are connected by a hinge.

10. A method of using a cosmetic product, comprising:
    using an applicator to deposit a drop of liquid or gel into a depression formed in the interior of a pressed cosmetic powder cake composed of hydrophobic material;
    depositing and maintaining the liquid within the depression of the pressed cosmetic powder cake to prevent the liquid from rolling off of the pressed powder cake;
    mixing the liquid with the pressed cosmetic powder cake with a mixing tool; and
    applying the mixed wet cosmetic product on a user.

11. The method of claim 10, wherein the mixing tool further includes the applicator.

* * * * *